United States Patent [19]
Nishizawa et al.

[11] Patent Number: 5,180,671
[45] Date of Patent: Jan. 19, 1993

[54] METHOD FOR PRODUCING OPTICALLY ACTIVE CYCLOPROPANE CARBOXYLIC ACID

[75] Inventors: Kanji Nishizawa; Satoshi Mitsuda; Ryohei Komaki; Masako Sugimoto, all of Hyogo; Chiaki Sugiki, Osaka; Yasutaka Ogami, Hyogo; Kazumi Sonoda, Hyogo; Fumitaka Kishimoto, Hyogo, all of Japan

[73] Assignee: Sumitomo Chemical Company, Limited, Osaka, Japan

[21] Appl. No.: 620,385
[22] PCT Filed: Apr. 16, 1987
[86] PCT No.: PCT/JP87/00244
  § 371 Date: Dec. 16, 1987
  § 102(e) Date: Dec. 16, 1987
[87] PCT Pub. No.: WO87/06269
  PCT Pub. Date: Oct. 22, 1987

Related U.S. Application Data

[63] Continuation of Ser. No. 143,848, Dec. 16, 1987, abandoned.

[30] Foreign Application Priority Data

Apr. 16, 1986 [JP] Japan .................................. 61-89803
Apr. 24, 1986 [JP] Japan .................................. 61-95444

[51] Int. Cl.$^5$ .......................... C12P 7/40; C07C 51/09
[52] U.S. Cl. .................................. 435/136; 435/280
[58] Field of Search ........................ 435/136, 280

[56] References Cited

U.S. PATENT DOCUMENTS 4,607,013 8/1986 Mitsuda et al. .................... 435/280
4,985,364 1/1991 Hildebrand et al. ................ 435/254

FOREIGN PATENT DOCUMENTS 0164573 12/1985 European Pat. Off. .
3418374 11/1985 Fed. Rep. of Germany ...... 435/136
9210892 11/1984 Japan .................................. 435/136
0199393 10/1985 Japan .................................. 435/136

OTHER PUBLICATIONS

*Chemical Abstracts* 102:202608q (Jun. 1985).
*Chemical Abstracts* 104:184884m (May 1986).
Tetrahedron Letters, vol. 26, pp. 407–410 (1985).
Angew. Chem. Int. Ed. Engl., vol. 23, pp. 67–68 (1984).

*Primary Examiner*—David M. Naff
*Assistant Examiner*—Jon P. Weber
*Attorney, Agent, or Firm*—Birch, Stewart, Kolasch & Birch

[57] ABSTRACT

The present relates to a process for preparing optically active cyclopropane carboxylic acid derivatives of salts thereof represented by the formula (III)

$$\begin{array}{c} CH_3 \quad CH_3 \\ \diagdown \quad \diagup \\ C \\ \diagup \quad \diagdown \\ X \diagdown \qquad C\text{———}C \\ \qquad C=C \diagup H \quad H \diagdown COOR' \\ X \diagup \quad H \end{array} \quad (III)$$

wherein X is chlorine atom, bromine atom, methyl group or trifluoromethyl group and R' is hydrogen atom or metal ion, by asymmetrically hydrolyzing cyclopropane carboxylic acid esters having the formula (II)

$$\begin{array}{c} CH_3 \quad CH_3 \\ \diagdown \quad \diagup \\ C \\ \diagup \quad \diagdown \\ X \diagdown \qquad C\text{———}C \\ \qquad C=C \diagup H \quad H \diagdown COOR \\ X \diagup \quad H \end{array} \quad (II)$$

wherein X is as defined above and R is $C_{1-4}$ alkyl group or halogen-substituted $C_{1-4}$ alkyl group with specific strains of microorganisms or esterase derived therefrom.

3 Claims, No Drawings

METHOD FOR PRODUCING OPTICALLY ACTIVE CYCLOPROPANE CARBOXYLIC ACID

This application is a continuation of application Ser. No. 07/143,848 filed on Dec. 16, 1987 which is now abandoned.

TECHNICAL FIELD

The present invention relates to a method for producing an optically active cyclopropane carboxylic acid. More particularly, the present invention relates to a method for producing optically active cyclopropane carboxylic acid derivatives or their salts represented by the following formula (I):

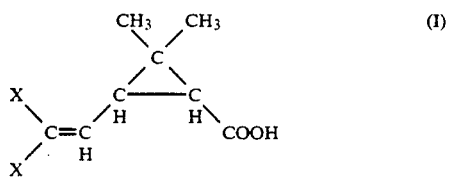

wherein X is as defined below, by asymmetric hydrolysis of cyclopropane carboxylic acid esters represented by the following formula (II):

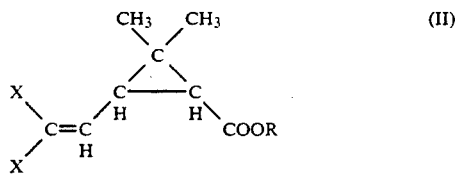

wherein X and R are as defined below, with microorganisms or esterases produced by the microorganisms.

BACKGROUND OF THE INVENTION

The cyclopropane carboxylic acids represented by the above formula (I) constitutes the acid moiety of a low toxic and rapidly acting insecticidal ester generally termed pyrethroid such as allethrin, permethrin, decamethrin, teffuluthrin, etc.

The cyclopropane carboxylic acids represented by the formula (I) contain two asymmetric carbon atoms at the 1-position and the 3-position and therefore have four diastereomers. Of these isomers, those having the absolute configurations of "1R, 3S" and "1R and 3R" are termed "(+)-cis isomer" and "(+)-trans isomer" (according to RS nomenclature), respectively, because the optical rotation of these isomers is (+) in a specific solvent and substitution groups of them are in a cis-form and a trans-form, respectively. And, the other two isomers having the absolute configurations of "1S, 3S" and "1S, 3R" are termed "(−)-cis isomer" and "(−)-trans isomer", respectively, because the optical rotation of these isomers is (−) in a specific solvent and substitution group of them are in a cis-form and a trans-form, respectively. Only the (+)-isomers have insecticidal activities as pyrethroid esters and the (−)-isomers have almost no insecticidal activities as pyrethroids.

The relative effects of the cis and the trans isomers vary according to the kinds of harmful insects to be killed and the type of effect.

It is possible to use the (+)-trans-pyrethroidal compound and (+)-cis- compound independently for different purposes. Accordingly, the production of (+)-cyclopropane carboxylic acids in effective manner is industrially important.

The presently known major method for production of (+)-isomers is organosynthetic optical resolution, but development of more economical methods for optical resolution is now desired for production of (+)-isomers because the organosynthetic optical resolution requires a relatively expensive optically active reagent or a complicated step. There are known methods for producing optically active (+)-trans acid by resolving cyclopropane carboxylates by asymmetric hydrolysis with a pig liver esterase (e.g., Schneider et al., Angewande chemie International Edition in English 23. 64 (1984)) or with a microbial esterase (Japanese Patent Publication (Kokai) No. 244295/1985).

However, the former method is industrially disadvantageous because of the expense and limited supply of the pig liver esterase. As for the latter method, it is reported that the trans-isomer of cyclopropane carboxylic acid ester is preferentially resolved by asymmetric hydrolysis but the method can not be industrially applied because the yield of (+)-trans-cyclopropane carboxylic acid is as low as 31 mg/100 ml culture medium, and the concentration of the substrate and the optical purity of the resulting (+)-trans cyclopropane carboxylic acid are low.

DISCLOSURE OF THE INVENTION

Under these circumstances, the inventors of this invention developed an industrially advantageous method for producing (+)-cyclopropane carboxylic acid (I). As a result, the inventors found that microorganisms belonging to the genera Rhodotorula, Rhodosporidium, Rhizomucor, Flammulina, Geotrichum, Aspergillus, Candida, Saccharomyces, Hansenula, Torulopsis, Rhodococcus, Penicillium, Dipodascus, Absidia, Streptomyces, Nocardia, Arthrobacter, Pseudomonas, Escherichia, Bacillus, Beauveria, Metschnikowia, Chromobacterium, Brevibacterium, Acinetobacter, Achromobacter, Kluyveromyces, Frateuria, Corynebacterium, Alcaligenes, Flavobacterium or Klebsiella, or an esterase produced by the above microorganisms specifically and preferentially hydrolyze (+)-cis-cyclopropane carboxylic acid esters represented by the formula (II):

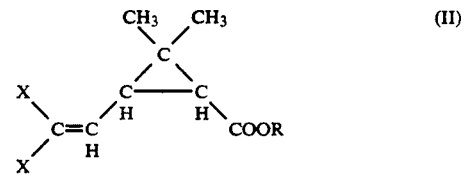

wherein X represents chlorine atom, bromine atom, methyl group or trifluoromethyl group and R represents $C_1$-$C_4$ alkyl group $C_1$-$C_4$ substituted by halogen atom, the configuration of the esters not being indicated by the formula, to produce optically active (+)-cis-cyclopropane carboxylic acid derivatives represented by the formula (III) or their salts:

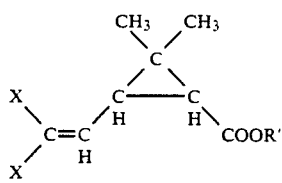

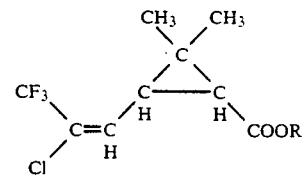

wherein X represents as above, R' represents hydrogen atom or metal ion, the configuration of the acid (I) not being indicated, and (—)-cis-cyclopropane carboxylic acid esters (II), and that the resulting (+)-cis-cyclopropane carboxylic acid derivatives or their salts are recoverable with high optical purity.

Especially, they found that, when (±)-cis-cyclopropane carboxylic acid esters represented by formula (II) wherein X represents chlorine atom, bromine atom, or methyl group and R represents alkyl group containing 1–4 carbon atoms are used as substrate, microorganisms belonging to the genera Rhodotorula, Rhodosporidium, Rhizomucor, Flammulina, Geotrichum, Candida, Hansenula, Torulopsis, Dipodascus, Arthrobacter, Pseudomonas, Escherichia, Bacillus, Beauveria, Metschnikowia, Chromobacterium, Brevibacterium, Acinetobacter, Achromobacter, Kluyveromyces, Frateuria, Flavobacterium, or Klebsiella or esterases produced by these microorganisms are advantageously applied to produce (+)-cis-cyclopropane carboxylic acids (I) or their salts with high optical purity.

Preferred examples of microorganisms which can selectively hydrolyze (+)-cis-cyclopropane carboxylic acid esters (II) to produce (+)-cis-cyclopropane carboxylic acids (I) are as follows:

| | |
|---|---|
| Rhodosporidium toruloides | IFO-0559 |
| Rhodosporidium toruloides | IFO-0871 |
| Rhodosporidium toruloides | IFO-8766 |
| Rhodotorula glutinis | IFO-1501 |
| Candida tropicalis | IFO-0618 |
| Hansenula anomala var. ciferii | IFO-0994 |
| Torulopsis candida | IFO-0768 |
| Arthrobacter citreus | IFO-12957 |
| Pseudomonas putida | IFO-12996 |
| Escherichia coli | IFO-13168 |
| Bacillus licheniforms | IFO-12195 |
| Flavobacterium capsulatum | IFO-12533 |
| Chromobacterium chocolatum | IFO-3758 |
| Achromobacter lyticus | ATCC-21456 |
| Rhizomucor pusillus | IFO-9856 |
| Flammulina velutipes | IFO-7046 |
| Geotrichum candidum | IFO-4597 |
| Dipodascus uninucleatus | ATCC-14626 |
| Beauveria bassiana | ATCC-26037 |
| Metschnikowia pulcherrima | IFO-0561 |
| Kluyveromyces lactis | IFO-1090 |
| Frateuria aurantia | IFO-3247 |
| Koebsiella pneumoniae | IFO-12059 |
| Pediococcus acidilactici | IFO-3076 |

It was also found that, in the case of optically active cis-cyclopropane carboxylic acid esters represented by the formula (IV):

wherein R represents an alkyl group containing 1–4 carbon atoms or an alkyl group containing 1–4 carbon atoms substituted by halogen atom, which does not indicate the configuration of the esters, optically active cis-cyclopropane carboxylic acid derivatives or its salts are produced with high optical purity by allowing the esters to react with microorganisms belonging to the genus Arthrobacter or Bacillus or esterases produced by these microorganisms to yield optically active (+)-cis-cyclopropane carboxylic acid and recovering it. Examples of microorganisms used for this purpose are Arthrobacter globiformis IFO-12958 and Bacillus sp. DC-1 (BP-FERM 1254).

It was further found that (±)-2,2-dimethyl-3(2,2-dichlorovinyl)cyclopropane carboxylic acid esters represented by formula (V):

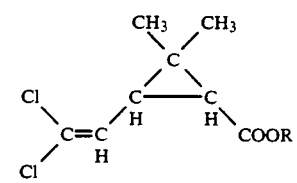

wherein R an alkyl group containing 1–4 carbon atoms or alkyl group containing 1–4 carbon atoms substituted by halogen atom, which does not indicate the configuration of the esters, are asymmetrically hydrolyzed effectively into (+)-trans-2,2-dimethyl-3(2,2-dichlorovinyl)cyclopropane carboxylic acid and ester of its diastereomer with the following microorganisms or esterase produced by the microorganisms:

| | |
|---|---|
| Arthrobacter globiformis | IFO-12958 |
| Thermomyces lanuginosus | IFO-9863 |
| Rhodotorula rubra | IFO-0918 |
| Rhodotorula rubra | IFO-1100 |
| Rhodotorula rubra | IFO-0889 |
| Rhodotorula rubra | IFO-0909 |
| Candida humicola | IFO-0760 |
| Candida lipolytica | NRRL-Y-6795 |
| Aspergillus oryzae | ATTC-14605 |
| Aspergillus flavus | ATTC-11492 and |
| Bacillus sp. DC-1 (BP-FERM 1254) | | and that (+)-trans-2,2- dimethyl-3(2,2-dichlorovinyl)-cyclopropane carboxylic acid or its salts are prepared with high optical purity.

In particular, it was confirmed that when Bacillus sp. DC-1, which is a microorganism isolated by the present inventors, is used, (+)-trans-2,2-dimethyl-3(2,2-dichlorovinyl)cyclopropane carboxylic acid or its salts are obtained with high optical purities at 10 bold higher levels (when compared in yields per 100 ml of culture medium) than the yields of conventional methods.

The present invention provides a method for producing optically active (+)-cis-cyclopropane carboxylic acid derivatives or their salts which comprises allowing (±)-cis-cyclopropane carboxylic acid esters represented by following formula (II):

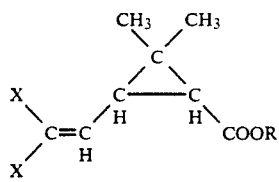

wherein X represents chlorine atom, bromine atom, methyl group or trifluoromethyl group, and R represents C₁-C₄ alkyl group or C₁-C₄ alkyl group substituted by halogen atom, which does not indicate the configuration of the ester, to react with microorganisms belonging to the genera Rhodotorula, Rhodosporidium, Rhizomucor, Flammulina, Geotrichum, Aspergillus, Candida, Saccharomyces, Hansenula, Torulopsis, Rhodococcus, Penicillium, Dipodascus, Absidia, Streptomyces, Nocardia, Arthrobacter, Pseudomonas, Escherichia, Bacillus, Beauveria, Metschnikowia, Chromobacterium, Brevibacterium, Acinetobacter, Achromobacter, Kluyveromyces, Frateuria, Corynebacterium, Alcaligenes, Flavobacterium, or Klebsiella or the esterases derived from these microorganisms, thereby asymmetrically hydrolyzing, with specificity and preference, (+)-cis-cyclopropane carboxylic acid esters of the formula (II) above to give optically active (+)-cis-cyclopropane carboxylic acid or their salts represented by formula (III):

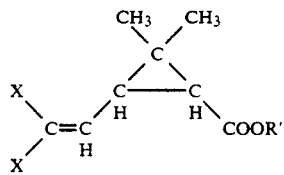

wherein X represents as above and R' represent hydrogen atom or metal ion, which does not indicate the configuration, and (−)-cis-cyclopropane carboxylic acid esters of the formula (II), and recovering the resulting optically active (+)-cis-cyclopropane carboxylic acids or their salts of the formula (I).

This invention also provides a method for producing (+)-cis-cyclopropane carboxylic acid derivative or its salts represented by the formula (VI):

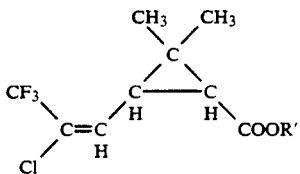

wherein R' represents hydrogen atom or metal ion, which does not indicate the configuration, which comprises allowing (±) -cis-cyclopropane carboxylic acid ester represented by the formula (IV)

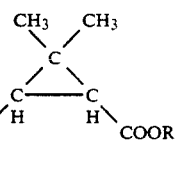

wherein R represents C₁-C₄ alkyl group or C₁-C₄ alkyl group substituted by halogen atoms, which does not indicate the configuration, to react with microorganisms belonging to the genus Arthrobacter or Bacillus or esterase produced by the above microorganisms and then recovering the resulting (+)-cis-cyclopropane carboxylic acid derivative or its salt of formula (I).

This invention further provides a method for producing (+)-trans-2,2-dimethyl-3(2,2-dichlorovinyl)cyclopropane carboxylic acid or its salts which comprises allowing (±)-2,2-dimethyl-3(2,2-dichlorovinyl)cyclopropane carboxylic acid ester represented by the formula (V):

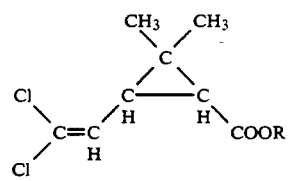

wherein R represents C₁-C₄alkyl group or C₁-C₄ alkyl group having halogen atom substituent, which does not indicate the configuration, to react with microorganisms selected from

*Arthrobacter globiformis* IFO-12958;
*Thermomyces lanuginosus* IFO-9863;
*Rhodotorula rubra* IFO-0918;
IFO-1100, IFO-0889, IFO-0909;
*Candida humicola* IFO-0760;
*Candida lipolytica* NRRL-Y-6795;
*Aspergillus oryzae* ATCC-14605;
*Aspergillus flavus* ATTC-11492; and
*Bacillus* sp. DC-1 (BP-FERM 1254)

or esterase produced by the above microorganisms until asymmetric hydrolysis is effected to produce (+)-trans-2,2-dimethyl-3(2,2-dichlorovinyl)cyclopropane carboxylic acid and diastereomer thereof and then recovering the resulting (+)-trans-2,2-dimethyl-3(2,2-dichlorovinyl)cyclopropane carboxylic acid or its salts.

The esters represented by the formula (II), which are starting materials in this invention, are easily obtained by well-known methods, for example, Pestic. Sci. Vol. 11, pp. 156-164 (1980). As the esters used as the starting materials, methyl ester, ethyl ester, propyl ester, butyl ester, monochloroethyl ester, monochloropropyl ester, monobromoethyl ester, etc. are conveniently used. Especially, methyl ester, ethyl ester, and monochloroethyl ester are advantageous because of commercial availability and ease in handling.

Example of salts of cyclopropane carboxylic acids represented by the formula (I) is alkali metal salt such as sodium salt.

Cultivation of the microorganisms is carried out in the usual procedure. For example, microorganisms are cultured in a liquid medium, for instance, inoculating microorganisms in a sterilized liquid medium and then cultivating usually at 20°-40° C., for 1-8 days with shaking. Alternatively, a solid medium may be used.

Any composition of the culture medium may be used, as long as the medium is familiar to cultivation of microorganisms and is utilizable by the microorganism used in this invention. As carbon sources and nitrogen sources in the medium, for example, glucose, starch, dextrin, molasses, fats and fatty oils, soybean powder, defatted soybean powder, fatty bean cake and corn steep liquor are employed. Ammonium sulfate, dipotassium hydrogenphosphate, magnesium sulfate and urea etc. may be used as inorganic salts in the medium. The cyclopropane carboxylic acid esters represented by the formula (II) or a fatty acid ester may be added to the medium.

In the method of this invention, asymmetric hydrolysis of cyclopropane carboxylic acid esters represented by the formula (II) is performed by mixing the esters (II) with a culture solution of the above microorganisms, a cell suspension, an esterase-containing aqueous solution such as a liquid esterase extract or its concentrated solution or their processed products, such as crude esterase, purified esterase etc., and then stirring or shaking the thus prepared mixture.

It is advantageous to perform the reaction at 10°-65° C. Since the stability of the esterase is likely to decrease at high temperature and the reaction rate is small at low temperatures, it is preferable that the reaction temperature be within the range of 20°-50° C. It is desirable that the pH of the mixture during reaction be 3-11, preferably around 5-10. It is preferable that buffers, such as phosphate buffer, be used to keep suitable pH during reaction.

Reaction time, which varies depending on the reaction conditions such as amount of esterase produced by the microorganisms, temperature during reaction, etc, is within the range of 2-3 to about 150 hours.

It is advantageous that the concentration of cyclopropane carboxylic acid esters represented by the formula (II) as a substrate when asymmetric hydrolysis is effected be 0.1-50 wt %, preferably 1-25 wt % based on a reaction liquid.

To the reaction mixture., 0.01-1% of surface active agents such as Triton X-100, Tween 80 or Brij 58 may be added, if necessary.

Cells of the microorganisms or the esterases may be used in the immobilized form, which is prepared by immobilizing them in a usual manner on inorganic or organic carriers, for example, zeolite, alumina, polysaccharide, polyamide, polystyrene resin, polyacrylic resin, and polyurethane resin, etc.

Cell suspension, suspension of ground cells or aqueous solution containing esterase, are prepared according to the usual method. Cell suspension is prepared by separating the cells harvested from culture medium by centrifugation or ultra filtration and suspending the cells in distilled water, ion-exchanged water, or buffer solution containing inorganic or organic salts, such as phosphate buffer solution. Suspension of ground cells is prepared by applying ultrasonic treatment, high pressure-breaking treatment by Manton-Gaulinhomogenizer or French Press or lytic enzyme treatment to the cell suspension. If necessary, the suspension may be changed to crude esterase solution by removing ground cell residue from the above suspension using centrifugation or ultrafiltration. Esterase is obtained from the suspension of ground cells by a conventional method, such as salting out with ammonium sulfate or sodium sulfate, or precipitation with organic solvents using hydrophilic organic solvents such as ethanol, propylalcohol, acetone, etc. Aqueous solution containing esterase is prepared by dissolving this obtained esterase in distilled water, ion-exchanged water, or buffer containing inorganic or organic salts, for example, phosphate buffer solution.

After the asymmetric hydrolysis is over, the liberated optically active cyclopropane carboxylic acid derivative represented by the formula (I) is separated from the unaltered ester and recovered by extraction with a solvent, column chromatography and fractional distillation, etc. For example, the reaction mixture is subjected to extraction with an organic solvent such as methyl isobutyl ketone, chloroform, ether, benzene or toluene and then the extract is subjected to fractional distillation under reduced pressure to separate the liberated optically active cyclopropane carboxylic acid derivatives represented by the formula (I) from the unaltered esters.

One of microorganisms utilized in this invention is Bacillus sp. DC-1, which is a novel microorganism and the characteristics of which are as follows.

(a) Morphological characteristics
1) From and size of cell: Rod, (0.5-0.6) $\mu m \times$ (1.2-1.7) $\mu m$. Occuring singly or in short chains.
2) Polymorphism: None
3) Motility: Motile by peritrichous flagella.
4) Spore formation: Endospores formed. Spherical or slightly oval with 0.4-0.6 $\mu m$ in diameter. Spores formed in a terminal position of the vegetative cell, having swell.
5) Gram staining: Negative
6) Acid fastness: Negative (b) Cultural characteristics on various mediums
1) Bouillon agar plate (35° C., 24 hours)
   Shape: Circular and projected form
   Margin: None
   Surface: Smooth and lustrous
   Color tone: Translucent and yellowish white
2) Bouillon agar slant (35° C., 24 hours)
   Growth degree: Moderate, growing like spread cloth or beads-like.
   Surface: Smooth and lustrous
   Color tone: Translucent and yellowish white
3) Bouillon liquid (35° C., 24 hours)
   Growth degree: Moderate
   Coloring/discoloring: None
   Pellicle: Not formed
   Sediment: Formed
4) Bouillon gelatine stab (35° C., 14 days) No liquefaction.
5) Litmus milk (35° C., 14 days) Slightly alkaline. No coagulation nor peptonization.

(c) Physiological characteristics: Cultured at 35° C. for 1-5 days. Negative ones were observed up to 14 days.
1) Reduction of nitrate: Positive Nitrite produced from nitrate.
2) Denitrification: Negative
3) MR test: Negative
4) VP test: Negative
5) Production of indole: Negative
6) Production of hydrogen sulfide: Negative
7) Hydrolysis of starch: Negative
8) Utilization of citric acid:
   Koser medium: Negative
   Christensen medium: Positive
9) Utilization of inorganic nitrogen sources:

Stanier et al's medium modified by Yamazato et al: (Yamazato et al. J. Gen. Appl. Microbiol. (1982) 28:195-213) Sodium succinate was used as the sole carbon source.

Nitrate: Not utilized
Ammonium salt: Utilized.
10) Pigmentation: Negative
11) Urease: Christensen urea medium: Positive
12) Oxidase: Positive
13) Catalase: Positive
14) Range of growth:
   Growth temperature: 10°-45° C. (optimum 30°-35° C.)
   Growth pH: 6.0-9.5 (optimum 8.5-9.0)
15) Anaerobic or aerobic growth: Aerobic
16) OF test: Negative
17) Production of acid or gas from saccharides:

|  | Acid | Gas |
|---|---|---|
| (1) L-arabinose | — | — |
| (2) D-xylose | — | — |
| (3) D-glucose | — | — |
| (4) D-mannose | — | — |
| (5) D-fructose | — | — |
| (6) D-galactose | — | — |
| (7) Maltose | — | — |
| (8) Sucrose | — | — |
| (9) Lactose | — | — |
| (10) Trehalose | — | — |
| (11) D-sorbitol | — | — |
| (12) D-mannitol | — | — |
| (13) Inositol | — | — |
| (14) Glycerin | — | — |
| (15) Starch | — | — |

Reference is made to Bergey's Manual of Determinative Bacteriology, 8th Ed (1974). The strain is identified as that belonging to genus Bacillus, since it is able to grow under aerobic conditions and forms endospores. The present strain is close to but different from *Bacillus sphaericus* and *Bacillus pasteurii,* as shown in the table below:

TABLE 1

| | the Present strain | *Bacillus sphaericus* | *Bacillus pasteurii* |
|---|---|---|---|
| Reduction of nitrate | + | − | − |
| Requirement of urea or ammonia | − | − | + |

In view of the above facts, the present inventors have recognized the strain to be a novel one belonging to genus Bacillus and nominated it Bacillus sp. DC-1. The strain was deposited with Fermentation Research Institute, Industrial Technology Agency, Japan (Address: 1-3, Higashi 1-chome, Yatabe-cho, Tukuba-Gun, Ibaragi, JAPAN) under FERM BP-1254. The strain was first deposited as FERM P-8719 on Mar. 31, 1986, then renumbered as FERM BP-1254 under Budapest Treaty on Jan. 12, 1987.

This invention will be explained more precisely according to the following examples. However, this invention is not restricted to these examples and usual modifications or improvements of these are within the scope of the present invention.

EXAMPLES 1-23

First, 100 ml each of the following liquid media was put in a 500 ml flask and sterilized: a malt-extract-yeast-extract medium (pH 6.5, prepared by dissolving 5.0 g of peptone, 10.0 g of glucose, 3.0 g of malt extract and 3.0 g of yeast extract in 1 l of water) for yeasts and fungi (examples 1-7 and 15-21,); a sugar broth medium (pH 7.2, prepared by dissolving 10.0 g of glucose, 5.0 g of peptone, 5.0 g of meat extract and 3.0 g of sodium chloride in 1 l of water) for bacteria and actinomycetes (examples 8-14, and 22-23). A loopful of cells of each microorganism shown in Table 1 growing on slant culture was inoculated in the medium and the mixture was subjected to shaking culture at 30° C. for 20 hours.

1.0 g of ethyl (±)-cis-2,2-dimethyl-3-(2,2-dichlorovinyl)cyclopropane carboxylate of formula (II), in which X represents chlorine atom and R represents ethyl group, was added to the medium above and the mixture was allowed to react with shaking at 30° C. for 40 hours. After the reaction was over, the pH of the reaction mixture was adjusted to 2 or lower with concentrated hydrochloric acid and the mixture was subjected to extraction with methyl isobutyl ketone. Next, an internal standard (dimethyl phthalate) was added to the extract and the mixture was analyzed by gas chromatography (column: 3% Thermon 3000, 1.1 m, 140° C.). Then, the yield of 2,2-dimethyl-3-(2,2-dichlorovinyl)cyclopropane carboxylic acid [in formula (I), X is Cl and R is H] and the recovery rate of the ethyl 2,2-dimethyl-3-(2,2-dichlorovinyl)cyclopropane carboxylate used as the starting material were calculated by comparing their peak areas with that of dimethyl phthalate. It was found that all of the remaining ethyl 2,2-dimethyl-3-(2,2-dichlorovinyl)cyclopropane carboxylate which was not converted to 2,2-dimethyl-3-(2,2-dichlorovinyl)cyclopropane carboxylic acid was recovered. After that, the extract was mixed with IN sodium hydroxide solution to extract 2,2-dimethyl-3-(2,2-dichlorovinyl)cyclopropane carboxylic acid as sodium salt into the aqueous layer. Next, the pH of the aqueous layer was adjusted to 2 or lower with HCl solution to liberate 2,2-dimethyl-3-(2,2-dichlorovinyl)-cyclopropane carboxylic acid which was then extracted by using methyl isobutyl ketone. After that, the extract was concentrated and evaporated to dryness to obtain substatially pure 2,2-dimethyl-3-(2,2-dichlorovinyl)cyclopropane carboxylic acid.

After 10 mg of thus produced 2,2-dimethyl-3-(2,2-dichlorovinyl)cyclopropane carboxylic acid was dissolved in 1 ml of toluene, equal molar amount each of thionyl chloride, pyridine and (+)-2-octanol were added and the mixture was allowed to react to produce diastereomers of ester of (+)-2-octanol and 2,2-dimethyl-3-(2,2-dichlorovinyl)cyclopropane carboxylic acid. Optical isomers assay in the diastereomers was performed by gas chromatography (column: 10% DCQF-1, 5.1 m, 180° C.).

The results are shown in the Table 10 in which the yield of 2,2-dimethyl-3-(2,2-dichlorovinyl)cyclopropane carboxylic acid represents the molar yield of 2,2-dimethyl-3-(2,2-dichlorovinyl)cyclopropane carboxylic acid relative to ethyl (+)-cis-2,2-dimethyl-3-(2,2-dichlorovinyl)cyclopropane carboxylate contained in ethyl (±)-cis-2,2-dimethyl-3-(2,2-dichlorovinyl)cyclopropane carboxylate used as the starting material.

EXAMPLES 24-27

The same reaction and analysis as used in Examples 1-23 were performed except that 1.0 g of ethyl (±)-cis-2,2-dimethyl-3-(2,2-dimethylvinyl)cyclopropane carboxylate represented by the formula (II) wherein X represents methyl group and R represents ethyl group, was used as a substrate.

As a result, (+)-cis-2,2-dimethyl-3-(2,2-dimethylvinyl)cyclopropane carboxylic acid represented by the formula (I) wherein X represents methyl group and R represents hydrogen atom, was obtained. The results are shown in the Table 11.

EXAMPLES 28-31

The same reaction and analysis as used in Example 1-23 were performed except that 1.0 g of methyl (±)-cis-2,2-dimethyl-3-(2,2-dibromovinyl)cyclopropane carboxylate represented by the formula (II) wherein X represents bromine atom and R represents methyl group, was used as a substrate to obtain (+)-cis-2,2-dimethyl-3-(2,2-dibromovinyl)cyclopropane carboxylic acid [in the formula (I), X is bromine atom and R is hydrogen atom]. The results are shown in the Table 12.

EXAMPLE 32

After 30 g of soluble starch, 7 g of polypeptone, 5 g of yeast extract and 5 g of potassium dihydrogenphosphate were dissolved in 1 l of distilled water, the pH of the solution was adjusted to 5.0 with 6N hydrochloric acid. After 10 ml of the above liquid medium was put in a test tube of 24 mm diameter and pluged with cotton, it was sterilized at 120° C. under high pressure for 15 minutes. A loopful of cell of Arthrobacter globiformis IFO-12958 was inoculated to the medium and subjected to shaking culture at 30° C. for 24 hours, which was used as seed culture. After 300 ml of a liquid medium having the same composition as above was put in a 2 l Sakaguchi's flask and sterilized in the same manner as above, 5 ml of the seed culture prepared as above was inoculated to the sterilized liquid medium and was subjected to shaking culture at 30° C. for 30 hours. After that, the resulting culture was centrifuged to harvest 5 g (wet weight) of cells. The cells were suspended in 20 ml of 0.3M NaOH-Na$_2$CO$_3$ buffer solution (pH 10) and then 0.1 g of ethyl (±)-cis-2,2-dimethyl-3-(2-chloro-3,3,3-trifluoropropenyl)cyclopropane carboxylate was added thereto. The mixture was allowed to react with stirring at 50° C. for 118 hours. Two ml of 35% hydrochloric acid was added to the reaction solution and the resulting mixture was applied to extraction with 50 ml of methyl isobutyl ketone. The extract was then analyzed by gas chromatography (column: Shinchrom F-51 (5%)+H$_3$PO$_4$(1%), 2.6 m, 185° C.) and the yield of cis-2,2-dimethyl-3-(2-chloro-3,3,3-trifluoropropenyl)cyclopropane carboxylic acid was calculated from the ratio of the peak area of this compound to that of ethyl cis-2,2-dimethyl-3(2-chloro-3,3,3-trifluoropropenyl)cyclopropane carboxylate. All of the starting ethyl cis-2,2-dimethyl-3(2-chloro-3,3,3-trifluoropropenyl)cyclopropane carboxylate were recovered in the form as it was excluding that which had been converted to cis-2,2-dimethyl-3(2-chloro-3,3,3-trifluoropropenyl)cyclopropane carboxylic acid. To the extract was added 1N sodium hydroxide solution to produce a sodium salt of cis-2,2-dimethyl-3(2-chloro-3,3,3-trifluoropropenyl)cyclopropane carboxylic acid and then this salt was extracted into an aqueous layer. The pH of the aqueous layer was adjusted with HCl solution to 2 or lower to liberate cis-2,2-dimethyl-3(2-chloro-3,3,3-trifluoropropenyl)cyclopropane carboxylic acid and this compound was extracted with methyl isobutyl ketone. The extract was concentrated to obtain almost pure cis-2,2-dimethyl-3(2-chloro-3,3,3-trifluoropropenyl)cyclopropane carboxylic acid.

After 5 mg of the above cis-2,2-dimethyl-3(2-chloro-3,3,3-trifluoropropenyl)cyclopropane carboxylic acid was dissolved in 1 ml of toluene, equal molar amount each of thionyl chloride, pyridine and 3,5-dichloroaniline were added and the mixture was allowed to react to produce an anilide, which was subjected to analysis for optical isomers by high performance liquid chromatography (column: SUMIPAX OA-2100, moving phase: n-hexane/dichloroethane=17/3, flow rate: 1.0 ml/minute). The results are shown in the following table. The hydrolysis rate shown in the table represents the molar ratio of the resulting cis-2,2-dimethyl-3(2-chloro-3,3,3-trifluoropropenyl)cyclopropane carboxylic acid to ethyl (±)-cis-2,2-dimethyl-3(2-chloro-3,3,3-trifluoropropenyl)cyclopropane carboxylate used as the starting material.

TABLE 2

| Hydrolysis rate (%) | Ratio of the isomers of the resulting cis-2,2-dimethyl-3(2-chloro-3,3,3-trifluoropropenyl)cyclopropane carboxylic acid. (+)-isomer/(−)-isomer |
|---|---|
| 8.7 | 100/0 |

EXAMPLE 33

After 10 g of soluble starch, 5 g of yeast extract, 5 g of polypeptone, 1 g of potassium dihydrogenphosphate and 0.2 g of magnesium sulfate heptahydrate were dissolved in 1 l of distilled water, the pH of the solution was adjusted to 9 with 10% sodium carbonate solution. After 10 ml of the thus prepared liquid medium was put in a test tube and sterilized in the same manner as in Example 32, a loopful of cells of Bacillus sp. DC-1 was inoculated into the sterilized liquid medium and was subjected to shaking culture at 30° C. for 24 hours to prepare a seed culture. After 300 ml of a liquid medium which was the same composition as above was put in a Sakaguchi's flask of 2 l capacity and sterilized in the same manner as above, 8 ml of the seed culture obtained as above was inoculated into the sterilized liquid medium and was subjected to shaking culture at 30° C. for 24 hours. After that, the resulting culture solution was centrifuged to harvest 2 g (wet weight) of cells, which were then suspended in 20 ml of 0.1M phosphate buffer solution (pH 8.0). To the suspension was added 0.1 g of monochloroethyl (±)-cis-2,2-dimethyl-3(2-chloro-3,3,3-trifluoropropenyl)cyclopropane carboxylate and the mixture was allowed to react with stirring at 40° C. for 120 hours. After that, the same operation as used in Example 32 was performed and the results shown in the following table were obtained.

TABLE 3

| Hydrolysis rate (%) | Ratio of the isomers of the resulting cis-2,2-dimethyl-3(2-chloro-3,3,3-trifluoropropenyl)cyclopropane carboxylic acid. (+)-isomer/(−)-isomer |
|---|---|
| 28.2 | 93.1/6.9 |

EXAMPLE 34

After 2 l of a liquid medium with the same composition as that used in Example 32 was put in a small fermentor and sterilized at 120° C. under high pressure for 15 minutes, 100 ml of the seed culture of Arthrobacter

*globiformis* IFO-12958 prepared in the same manner as in Example 32 was inoculated into the sterilized medium and was subjected to aeration stirring culture at 30° C. for 24 hours. Following that, the resulting cultured solution was centrifuged to harvest 53 g (wet weight) of cells. After the above harvested cells were suspended in 200 ml of 0.1M NaOH—Na$_2$CO$_3$ buffer solution (pH 10), the cells were then ground using a French press (product of the American Amico Company) and the cell debris were removed by centrifugation to obtain a crude enzyme solution. The resulting crude enzyme solution was then subjected to ammonium sulfate fractionation to collect a 30–60% saturation fraction and this fraction was lyophilized to obtain 1.3 g of a crude enzyme powder. After 0.5 g of the above crude enzyme powder was dissolved in 20 ml of 0.3 NaOH—Na$_2$CO$_3$ buffer solution (pH 10), 0.1 g of monochlorethyl (±)-cis-2,2-dimethyl-3-(2-chloro-3,3,3-trifluoropropenyl)cyclopropane carboxylate was added to the solution and the resulting mixture was allowed to react with string at 50° C. for 117 hours. Two ml of 35% hydrochloric acid was added to the reaction mixture and the mixture was subjected to extraction with 50 ml of methyl isobutyl ketone. After that, the same operation as used in Example 32 was performed and the results shown in the following table were obtained.

TABLE 4

| Hydrolysis rate (%) | Ratio of the isomers of the resulting cis-2,2-dimethyl-3(2-chloro-3,3,3-trifluoropropenyl)cyclopropane carboxylic acid. (+) isomer/(−)-isomer |
|---|---|
| 24.4 | 99.0/1.0 |

EXAMPLE 35

After 30 g of soluble starch, 7 g of polypeptone, 5 g of yeast extract and 5 g of potassium dihydrogenphosphate were dissolved in 1 l of distilled water, the pH of the solution was adjusted to 5.0 with 6N hydrochloric acid. After 10 ml of the above liquid medium was put in a test tube of 24 mm diameter, which was then pluged with cotton, it was sterilized at 120° C. under high pressure for 15 minutes a loopful of cells of *Arthrobacter globiformis* IFO-12958 was inoculated into the medium and was subjected to shaking culture at 30° C. for 24 hours to prepare a seed culture. After 300 ml of a liquid medium which has the same composition as above was put in a Sakaguchi's flask of 2 l capacity and sterilized in the same manner as above, 5 ml of the seed culture prepared as above was inoculated into the sterilized liquid medium and was subjected to shaking culture at 30° C. for 30 hours. After that, the resulting cultured solution was centrifuged to obtain 5 g (wet weight) of cells which were then suspended in 20 ml of 0.3M NaOH—Na$_2$CO$_3$ buffer solution (pH 10). To the suspension was added 1.0 g of ethyl (±)-cis, trans-2,2-dimethyl-3(2,2-dichlorovinyl)cyclopropane carboxylate (cis/trans ratio=45/55) and the mixture was allowed to react with stirring at 50° C. for 48 hours. Two ml of 35% hydrochloric acid was added to the reaction solution and the resulting mixture was subjected to extraction with 50 ml of methyl isobutyl ketone.

The extract was then analyzed by gas chromatography (column: Shinchrom F-51 (5%)+H$_3$PO$_4$ (1%), 2.6 m, 185° C.) and the yield of 2,2-dimethyl-3(2,2-dichlorovinyl)cyclopropane carboxylic acid was calculated from the ratio of the peak area of this compound to that of ethyl 2,2-dimethyl-3(2,2-dichlorovinyl)cyclopropane carboxylate. All of the starting ethyl 2,2-dimethyl-3-(2,2-dichlorovinyl)cyclopropane carboxylate were recovered as it was excluding that which has been converted to 2,2-dimethyl-3(2,2-dichlorovinyl)cyclopropane carboxylic acid. 1N sodium hydroxide solution was added to the extract to transfer 2,2-dimethyl-3(2,2-dichlorovinyl) cyclopropane carboxylic acid as a sodium salt into an aqueous layer. The pH of the aqueous layer was adjusted to 2 or lower with hydrochloric acid to liberate 2,2-dimethyl-3(2,2-dichlorovinyl)cyclopropane carboxylic acid and this compound was extracted with methyl isobutyl ketone. The extract was concentrated and evaporated to dryness to obtain almost chemically pure 2,2-dimethyl-3(2,2-dichlorovinyl)cyclopropane carboxylic acid.

After 5 mg of thus obtained 2,2-dimethyl-3(2,2-dichlorovinyl)cyclopropane carboxylic acid was dissolved in 1 ml of toluene, equal molar amount each of thionyl chloride, pyridine and 3,5-dichloroaniline were added and allowed to react to produce anilide. The relative concentrations of isomers of 2,2-dimethyl-3(2,2-dichlorovinyl)cyclopropane carboxylic acid were determined by analyzing the resulting anilide by high performance liquid chromatography (column: SUMIPAX OA 2100, moving phase: n-hexane/dichloroethane=17/3, flow rate: 1.0 ml/minute). The results are shown in the following Table 13.

The hydrolysis rate shown in the table represents the molar ratio of the resulting 2,2-dimethyl-3(2,2-dichlorovinyl)cyclopropane carboxylic acid to ethyl (±)-cis, trans-2,2-dimethyl-3(2,2-dichlorovinyl)cyclopropane carboxylate used as the starting material.

TABLE 5

| Hydrolysis rate (%) | Ratio of the isomers of the resulting 2,2-dimethyl-3(2,2-dichlorovinyl)cyclopropane carboxylic acid (+)-cis isomer/(−)-cis isomer/ (+)-trans isomer/(−)-trans isomer |
|---|---|
| 22.8 | 0:0:100:0 |

EXAMPLE 36

A medium was prepared by dissolving 20 g of glucose, 50 g of corn steep liquor, 2 g of potassium dihydrogenphosphate, 1 g of magnesium sulfate heptahydrate, 5 g of calcium carbonate and 5 g of ethyl butyrate in 1 l of distilled water, the pH of which was adjusted to 6.0 with 6N hydrochloric acid. After 10 ml of the above liquid medium was put in a test tube and sterilized in the same manner as Example 35, a loopful of cells of *Thermomyces lanuginosus* IFO-9863 was inoculated into the sterilized medium and was subjected to shaking culture at 45° C. for 48 hours to give a seed culture. After 300 ml of a liquid medium which was the same composition as above was put in a Sakaguchi's flask of 2 l capacity and sterilized in the same manner as above, 8 ml of the seed culture prepared as above was inoculated into the sterilized liquid medium and was subjected to shaking culture at 45° C. for 48 hours. The resulting cultured solution was centrifuged to collect cells which were then washed with 50 ml of distilled water. To the washed cells was added 50 ml of 0.1M phosphate buffer solution (pH 8.0) and they were ground by ultrasonic treatment.

After the resulting liquid solution containing ground cells was centrifuged and the supernatant was collected, it was concentrated three times using an ultrafilter. To the concentrated supernatant was added 1.0 g of ethyl (±)-cis, trans-2,2-dimethyl-3(2,2-dichlorovinyl)cyclopropane carboxylate (cis/trans ratio=45/55) and the mixture was allowed to react with stirring at 40° C. for 72 hours. Following that, the same operation as used in Example 35 was performed and the following results were obtained.

TABLE 6

| Hydrolysis rate (%) | Ratio of the isomers of the resulting 2,2-dimethyl-3(2,2-dichlorovinyl)cyclopropane carboxylic acid (+)-cis-isomer/(−)cis-isomer/ (+)-trans-isomer/(−)-trans-isomer |
|---|---|
| 9.5 | 0:0:96.7:3.3 |

EXAMPLE 37

After 2 l of a liquid medium having the same composition as the one used in Example 35 was put in a small fermentor and sterilized at 120° C. under high pressure for 15 minutes, 100ml of a seed culture of *Arthrobacter flobiformis* IFO-12958 prepared in the same manner as Example 35 was inoculated into the sterilized liquid medium and was subjected to airation agitation culture at 30° C. for 24 hours. Following that, the cultured solution was centrifuged to harvest 53 g (wet weight) of cells. After the harvested cells were suspended in 200 ml of 0.3M NaOH—Na$_2$CO$_3$ buffer solution (pH 10), the cells were ground using a French press (product of the American Amico Company) and the ground cells were removed by centrifugation to obtain a crude enzyme solution. The crude enzyme solution was then subjected to ammonium sulfate fractionation to collect a 30–60% saturation fraction and this was lyophilized to obtain 1.3 g of a crude enzyme powder. After 0.5 g of the crude enzyme powder was dissolved in 20 ml of 0.1M NaOH—Na$_2$CO$_3$ buffer solution (pH 10), 2.0 g of monochloroethyl (±)-cis,trans-2,2-dimethyl-3(2,2-dichlorovinyl)cyclopropane carboxylate (cis/trans ratio=45/55) was added to the solution and the resulting mixture was allowed to react with stirring at 50° C. for 17 hours. To the reaction mixture was added 2 ml of 35% hydrochloric acid and the mixture was subjected to extraction with 50 ml of methyl isobutyl ketone. After that, the same operation used in Example 35 was performed and the following results were obtained.

TABLE 7

| Hydrolysis rate (%) | Ratio of the isomers of the resulting 2,2-dimethyl-3(2,2-dichlorovinyl)cyclopropane carboxylic acid (+)-cis isomer/(−)-cis isomer/ (+)-trans isomer/(−)-trans isomer |
|---|---|
| 18.0 | 11.1:0:88.9:0 |

EXAMPLE 38

A medium was prepared by dissolving 5 g of yeast extract, 5 g of polypeptone, 1 g of potassium dihydrogenphosphate and 0.2 g of magnesium sulfate (heptahydrate) in 1 l of distilled water, the pH of which was adjusted to 9.0 with 10% sodium carbonate solution. After 10 ml of the above liquid medium put in a test tube of 24 mm diameter was sterilized with steam at 120° C. under high pressure for 15 minutes, a loopful of cells of Bacillus sp. DC-1 was inoculated into the sterilized liquid medium and was subjected to shaking culture at 30° C. for 24 hours to prepare a seed culture. After 100 ml of a liquid medium which has the same composition as above was put in an Erlenmeyer flask of 500 ml capacity and sterilized in the same manner as above, 1 ml of the seed culture prepared as above was inoculated with the sterilized liquid medium and was subjected to shaking culture at 30° C. for 24 hours. To the cultured solution was added 1.5 g of ethyl (±)-cis,trans-2,2-dimethyl-3(2,2-dichlorovinyl)cyclopropane carboxylate (cis/trans ratio=45/55) and the mixture was allowed to react with shaking at 30° C. and 120 hours. To the resulting reaction solution was added 1 ml of 35% HCl solution and the resulting mixture was subjected to extraction with 50 ml of methyl isobutyl ketone. The extraction layer was analyzed by gas chromatography (column: 3% Thermon 3000, 1.1 m, 140° C.) and the yield of 2,2-dimethyl-3-(2,2-dichlorovinyl)cyclopropane carboxylic acid was calculated from the ratio of the peak area of this compound to that of ethyl 2,2-dimethyl-3-(2,2-dichlorovinyl)cyclopropane carboxylate. All of the starting ethyl 2,2-dimethyl-3-(2,2-dichlorovinyl)cyclopropane carboxylate were recovered excluding that which had been converted to 2,2-dimethyl-3-(2,2-dichlorovinyl)cyclopropane carboxylic acid.

To the extract was added 1N sodium hydroxide solution to transfer 2,2-dimethyl-3(2,2-dichlorovinyl)-cyclopropane carboxylic acid as sodium salt into the aqueous layer. The pH of the aqueous layer was adjusted to 2 or lower with HCl solution to liberate 2,2-dimethyl-3(2,2-dichlorovinyl)cyclopropane carboxylic acid from the sodium salt and the liberated 2,2-dimethyl-3-(2,2-dichlorovinyl)cyclopropane carboxylic acid was extracted with methyl isobutyl ketone. The liquid extract was concentrated and evaporated to dryness, thereby 0.404 g of almost chemically pure 2,2-dimethyl-3-(2,2-dichlorovinyl)cyclopropane carboxylic acid (permetric acid) was obtained.

After 5 mg of the above 2,2-dimethyl-3-(2,2-dichlorovinyl)cyclopropane carboxylic acid was dissolved in 1 ml of toluene, equal molar amount each of thionyl chloride, pyridine and 3,5-dichloroaniline were added and allowed to react to produce anilide which was analyzed to determine the relative concentrations of the isomers of 2,2-dimethyl-3-(2,2-dichlorovinyl)cyclopropane carboxylic acid by high performance liquid chromatography (column: SUMIPAX OA-2100, moving phase: n-hexane/dichloroethane=17/3(V/V), flow rate: 1.0 ml/min.). The results are shown in the following table, in which the yield represents the molar yield of (+)-trans-2,2-dimethyl-3(2,2-dichlorovinyl)cyclopropane carboxylic acid to ethyl (+)-trans-2,2-dimethyl-3-(2,2-dichlorovinyl)cyclopropane carboxylate contained in the starting material.

TABLE 8

| Yield, (%) | Ratio of the isomers of the resulting permethric acid (+)-trans isomer/(−)-trans isomer/(+)-cis isomer/(−)-cis isomer |
|---|---|
| 100 | 90.1:9.9:0:0 |

EXAMPLE 39

Bacillus sp. DC-1 was cultivated in the same manner as in Example 38 and 0.5 g (wet weight) of cells was obtained from 100 ml of the cultured solution by centrifugation. After the harvested cells were suspended in 10 ml of 0.1M phosphate buffer solution (pH 8.0), 1.0 g of methyl (±)-cis, trans-2,2-dimethyl-3-(2,2-dichlorovinyl)cyclopropane carboxylate (cis/trans ratio=45/55) was added to the suspension and the mixture was stirred at 30° C. for 96 hours. Extraction and isolation from the resulting mixture was performed in the same manner as in Example 38, thereby 0.277 g of 2,2-dimethyl-3-(2,2-dichlorovinyl)cyclopropane carboxylic acid was obtained. All of the starting methyl 2,2-dimethyl-3-(2,2-dichlorovinyl)cyclopropane carboxylate were recovered as it was excluding that which had been converted to 2,2-dimethyl-3(2,2-dichlorovinyl)cyclopropane carboxylic acid.

Analysis was effected in the same manner as in Example 38 and the following results were obtained. In the table, the yield represents the molar yield of (+)-trans-2,2-dimethyl-3-(2,2-dichlorovinyl)cyclopropane carboxylic acid to methyl (+)-trans-2,2-dimethyl-3-(2,2-dichlorovinyl)cyclopropane carboxylate contained in the starting material

TABLE 9

| Yield (%) | Ratio of the isomers in permethric acid (+)-trans isomer/ (−)-trans isomer/ (+)-cis-isomer/ (−)-cis isomer |
|---|---|
| 100 | 93.0:7.0:0:0 |

EXAMPLES 40–47 malt extract and 3.0 g of yeast extract in 1 l of water) was put in a 500 ml flask and sterilized, a loopful of cells of the microorganism each shown in the Table 4 was inoculated from slant culture into the sterilized liquid medium and was subjected to shaking culture at 30° C. for 20 hours. To the cultured solution was added 1.0 g of ethyl (±)-cis, trans-2,2-dimethyl-3(2,2-dichlorovinyl)cyclopropane carboxylate (cis/trans ratio=45/55) and the mixture was reciprocally shaked at 30° C. for 72 hours. Extraction, isolation and analysis of the resulting culture were performed in the same manner as in Example 38 to obtain almost chemically pure 2,2-dimethyl-3-(2,2-dichlorovinyl)cyclopropane carboxylic acid (permethric acid). All of the ethyl 2,2-dimethyl-3-(2,2-dichlorovinyl)cyclopropane carboxylate added were recovered as it was excluding that which has been converted to 2,2-dimethyl-3-(2,2-dichlorovinyl)cyclopropane carboxylic acid. The analytical results of the reaction performed by each bacterial strain are shown in Table 4. In the table, the yield represents the molar yield of (+)-trans-2,2-dimethyl-3-(2,2-dichlorovinyl)cyclopropane carboxylic acid to ethyl (+)-trans-2,2-dimethyl-3-(2,2-dichlorovinyl)cyclopropane carboxylate contained in the starting material.

TABLE 10

| example | microorganism cultured | | Cis-2,2-dimethyl-3-(2,2-dichlorovinyl)cyclopropane carboxylic acid | |
|---|---|---|---|---|
| | | | Yield (%) | (+)-isomer/(−)-isomer |
| 1 | Rhodosporidium toruloides | IFO-0559 | 29.6 | 100/0 |
| 2 | Rhodosporidium toruloides | IFO-0871 | 22.8 | 100/0 |
| 3 | Rhodosporidium toruloides | IFO-8766 | 16.1 | 100/0 |
| 4 | Rhodotorula glutinis | IFO-1501 | 15.3 | 95.9/4.1 |
| 5 | Candida tropicalis | IFO-0618 | 4.10 | 92.0/8.0 |
| 6 | Hansenula anomala var. ciferii | IFO-0994 | 8.00 | 91.0/9.0 |
| 7 | Torulopsis candida | IFO-0768 | 11.0 | 85.0/15.0 |
| 8 | Arthrobacter citreus | IFO-12957 | 6.50 | 92.0/8.0 |
| 9 | Pseudomonas putida | IFO-12996 | 6.48 | 89.1/10.9 |
| 10 | Escherichia coli | IFO-13168 | 2.41 | 93.5/6.5 |
| 11 | Bacillus licheniformis | IFO-12195 | 4.14 | 90.0/10.0 |
| 12 | Flavobacterium capsulatum | IFO-12533 | 6.39 | 88.2/11.8 |
| 13 | Chromobacterium chocolatum | IFO-3758 | 0.84 | 96.7/3.3 |
| 14 | Achromobacter lyticus | ATCC-21456 | 2.16 | 95.4/4.6 |
| 15 | Rhizomucor pusillus | IFO-9856 | 2.84 | 95.2/4.8 |
| 16 | Flammulina velutipes | IFO-7046 | 1.56 | 91.1/8.9 |
| 17 | Geotrichum candidum | IFO-4597 | 6.28 | 88.3/11.7 |
| 18 | Dipodascus uninucleatus | ATCC-14626 | 3.22 | 85.4/14.6 |
| 19 | Beauveria bassiana | ATCC-26037 | 1.80 | 89.4/10.6 |
| 20 | Metschnikowia pulcherrima | IFO-0561 | 4.20 | 98.2/1.8 |
| 21 | Kluyveromyces lactis | IFO-1090 | 0.48 | 99.1/0.9 |
| 22 | Frateuria aurantia | IFO-3247 | 3.96 | 88.0/12.0 |
| 23 | Klebsiella pneumoniae | IFO-12059 | 3.96 | 79.1/20.9 |

TABLE 11

| example | microorganism cultured | | Cis-2,2-dimethyl-3-(2,2-dimethylvinyl)cyclopropane carboxylic acid | |
|---|---|---|---|---|
| | | | Yield (%) | (+)-isomer/(−)-isomer |
| 24 | Rhodosporidium toruloides | IFO-0559 | 25.4 | 100/0 |
| 25 | Rhodosporidium toruloides | IFO-0871 | 19.9 | 100/0 |
| 26 | Rhodosporidium toruloides | IFO-8766 | 17.8 | 100/0 |
| 27 | Rhodotorula glutinis | IFO-1501 | 13.3 | 97.3/2.7 |

After 100 ml of a liquid medium (pH 6.5, prepared by dissolving 5.0 g of peptone, 10.0 g of glucose, 3.0 g of

TABLE 12

| example | microorganism cultured | | Cis-2,2-dimethyl-3-(2,2-dibromovinyl)cyclopropane carboxylic acid | |
|---|---|---|---|---|
| | | | Yield (%) | (+)-isomer/(−)-isomer |
| 28 | Rhodosporidium toruloides | IFO-0559 | 31.1 | 100/0 |
| 29 | Rhodosporidium toruloides | IFO-0871 | 18.4 | 100/0 |
| 30 | Rhodosporidium toruloides | IFO-8766 | 19.3 | 100/0 |

TABLE 12-continued

| | | Cis-2,2-dimethyl-3-(2,2-dibromo-vinyl)cyclopropane carboxylic acid | |
|---|---|---|---|
| example | microorganism cultured | Yield (%) | (+)-isomer/(−)-isomer |
| 31 | Rhodotorula glutinis IFO-1501 | 15.5 | 96.4/3.6 |

TABLE 13

| | | | Ratio of isomers of permethric acid |
|---|---|---|---|
| example | microorganism cultured | Yield (%) | (+)-trans-isomer/(−)-trans-isomer/ (+)-cis-isomer/(−)-cis-isomer |
| 40 | Rhodotorula rubra | IFO-0918 | 44.0 | 98.7/1.3/0/0 |
| 41 | Rhodotorula rubra | IFO-1100 | 40.2 | 98.2/1.8/0/0 |
| 42 | Rhodotorula rubra | IFO-0889 | 32.6 | 95.4/4.6/0/0 |
| 43 | Rhodotorula rubra | IFO-0909 | 20.00 | 96.0/4.0/0/0 |
| 44 | Candida humicola | IFO-0760 | 12.40 | 100/0/0/0 |
| 45 | Candida lipolytica | NRRL-Y-6795 | 11.6 | 91.3/8.7/0/0 |
| 46 | Aspergillus oryzae | ATCC-14605 | 63.0 | 100/0/0/0 |
| 47 | Aspergillus flavus | ATCC-11492 | 12.3 | 100/0/0/0 |

What is claimed is:

1. A process for producing an optically active (+)-cis-cyclopropane carboxylic acid or derivatives thereof, which comprises allowing a (±)-cis-cyclopropane carboxylic acid ester represented by formula (IV),

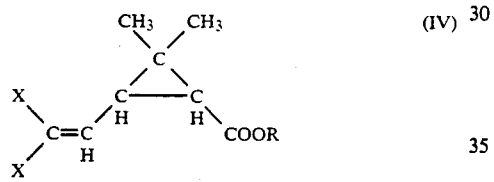

wherein X is selected from the group consisting of a chlorine atom, a bromine atom, a methyl group, and a trifluoromethyl group, and R is selected from the group consisting of a $C_1$-$C_4$ alkyl group and a $C_1$-$C_4$ alkyl group substituted with a halogen atom, to react with a microorganism selected from the group consisting of

| Rhodosporidium toruloides | IFO-0559, |
|---|---|
| Rhodosporidium toruloides | IFO-0871, |
| Rhodosporidium toruloides | IFO-8766, |
| Rhodotorula glutinis | IFO-1501, |
| Hansenula anomala var. ciferii | IFO-0994, |
| Torulopsis candida | IFO-0768, |
| Arthrobacter citreus | IFO-12957, |
| Pseudomonas putida | IFO-12996, |
| Escherichia coli | IFO-13168, |
| Bacillus licheniformis | IFO-12195, |
| Flavobacterium capsulatum | IFO-12533, |
| Achromobacter lyticus | ATTC-21456, |
| Thizomucor pusillus | IFO-9856, |
| Flammulina velutipes | IFO-7046, |
| Geotrichum candidum | IFO-4597, |
| Dipodascus uninucleatus | ATTC-14626, |
| Beauveria bassiana | ATTC-26037, |
| Metschnikowia pulcherrima | IFO-0561, |
| Kluyveromyces lactis | IFO-1090, |
| Frateuria aurantia | IFO-3247, and |
| Klebsiella pneumoniae | IFO-12059, | or an esterase produced thereby which can selectively and asymmetrically hydrolyze a (±)-cis-cyclopropane carboxylic acid ester of formula (IV), to produce an optically active (+)-cis-cyclopropane carboxylic acid or derivatives thereof represented by formula (III),

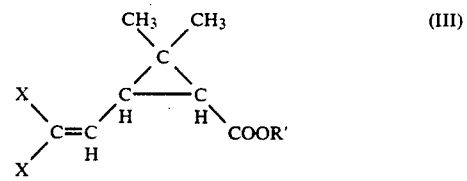

wherein X is as above, and R' is selected from the group consisting of hydrogen atom and a metal ion, and a (−)-cis-cyclopropane carboxylic acid ester of formula (IV), and then recovering said optically active (+)-cis-cyclopropane carboxylic acid or derivatives thereof represented by formula (III).

2. A process for producing a (+)-cis-cyclopropane carboxylic acid or derivatives thereof represented by formula (V),

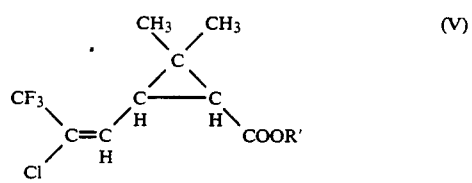

wherein R' is selected from the group consisting of a hydrogen atom and a metal ion, which comprises allowing a (±)-cis-cyclopropane carboxylic acid ester of formula (VI),

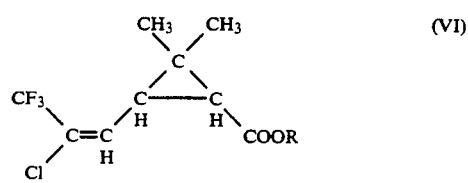

wherein R is selected from the group consisting of a $C_1$-$C_4$ alkyl group and a $C_1$-$C_4$ alkyl group substituted by a halogen atom, to react with Arthrobacter globiformis IFO-12958 or an esterase produced thereby which can perform this hydrolysis, and then recovering said (+)-cis-cyclopropane carboxylic acid or derivatives thereof represented by formula (V).

3. A process for producing a (+)-trans-2,2-dimethyl-3-(2,2-dichlorovinyl)cyclopropane carboxylic acid or salts thereof, which comprises allowing a (±)-2,2-dimethyl-3-(2,2-dichlorovinyl)cyclopropane carboxylic acid ester represented by formula (VIII),

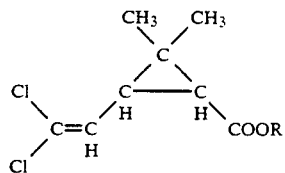

wherein R is selected from the group consisting of a $C_1$–$C_4$ alkyl group and a $C_1$–$C_4$ alkyl group substituted with a halogen atom, to react with *Arthrobacter globiformis* IFO-12958 or an esterase produced thereby which can perform this hydrolysis, to asymmetrically hydrolyze said ester thereby forming said (+)-trans-2,2-dimethyl-3-(2,2-dichlorovinyl)cyclopropane carboxylic acid salts thereof and the ester of its diastereomer, and then recovering said (+)-trans-2,2-dimethyl-3-(2,2-dichlorovinyl)cyclopropane carboxylic acid or salts thereof.

* * * * *